United States Patent [19]

Sawyer et al.

[11] Patent Number: 4,568,333
[45] Date of Patent: Feb. 4, 1986

[54] VALVE ARRANGEMENT ESPECIALLY SUITABLE FOR PREVENTING INTRODUCTION OF AIR INTO VASCULAR SYSTEMS

[76] Inventors: Philip N. Sawyer, 7600 Ridge Blvd., Brooklyn, N.Y. 11209; Joseph Fitzgerald, 168 Bank 147th St., Newport, N.Y. 11694

[21] Appl. No.: 511,256

[22] Filed: Jul. 6, 1983

Related U.S. Application Data

[63] Continuation-in-part of Ser. No. 484,205, Apr. 12, 1983.

[51] Int. Cl.[4] ............................................. A61M 5/00
[52] U.S. Cl. .................................. 604/122; 137/493; 137/860; 604/129
[58] Field of Search ............ 137/516.11, 860, DIG. 4, 137/493; 251/5; 604/8–10, 129, 122

[56] References Cited

U.S. PATENT DOCUMENTS

| | | | |
|---|---|---|---|
| 2,786,642 | 3/1957 | Comb | 251/5 X |
| 2,988,103 | 6/1961 | Canvasser | 251/5 X |
| 3,298,391 | 1/1967 | Savage | 251/5 X |
| 3,769,982 | 11/1973 | Schulte | 604/10 |
| 3,833,013 | 9/1974 | Leonard | 604/122 X |
| 3,991,768 | 11/1976 | Portnoy | 604/10 |
| 4,324,239 | 4/1982 | Gordon et al. | 604/122 |

FOREIGN PATENT DOCUMENTS 555251 6/1977 U.S.S.R. ............................ 137/860

Primary Examiner—Dalton L. Truluck
Attorney, Agent, or Firm—Pennie & Edmonds

[57] ABSTRACT

A flow control device which consists of a tubular body having radial sets of orifices therein covered by a resilient member which defines an annular space to which the orifices are connected. The resilient member permits positive pressure to drive fluid through the orifices but prevents negative pressure from sucking air through the orifices. A spring urges the resilient member against one of the sets of orifices.

21 Claims, 3 Drawing Figures

VALVE ARRANGEMENT ESPECIALLY SUITABLE FOR PREVENTING INTRODUCTION OF AIR INTO VASCULAR SYSTEMS

OTHER APPLICATIONS

This application is a continuation-in-part of application Ser. No. 484,205 filed Apr. 12, 1983.

FIELD OF INVENTION

This invention relates to valve arrangements and, more particularly, to valve arrangements suitable for preventing the entry of air into patients' vascular systems during intravenous procedures.

BACKGROUND

Valve arrangements have long been known which are suitable for monitoring the control of fluid flow through tubs in various types of procedures and in various types of apparatus as described in my co-pending application Ser. No. 484,205, filed Apr. 12, 1983.

Procedures have long been known involving the introduction of fluids into the vascular systems of patients. These have developed to a point of employing a source of fluid for intravenous procedures and connecting such source via a pump through a needle or catheter into the vascular system. The pump itself has been developed to a point that when connecting catheters are accidentally opened to ambient atmosphere, the pumping operation is terminated thereby to reduce the possibilities of air being introduced into the vascular system. This is necessary because the introduction of air will cause an embolism which in turn may be fatal to the patient being treated. Nevertheless, the use of such a pump, which is commercially available, is not always effective to prevent accidents of the aforenoted typed in all cases. Thus, for example, when the intravenous tubing is coupled to a catheter on the down stream side of the pump, and this catheter becomes accidentally opened to ambient atmosphere, the pressure differential between ambient atmosphere and the vascular system in which the distal tip of the catheter resides is such as to cause air to be sucked through the catheter into the vascular system. This accidental occurrence has been known to cause serious harm to the patient being treated. A number of patents have been found to deal with intravenous procedures and problems of the aforenoted type, as well as to related systems exposed to pressure differential or the like. These patents include U.S. Pat. Nos. 2,538,662; 3,570,808; 3,599,670; 3,888,249; 4,103,686; 4,252,166; 4,324,239; and 4,335,747.

C. Abbott in U.S. Pat. No. 2,538,662 discloses a surgical apparatus for the intravenous administration of liquids, such as whole blood, blood plasma, destrose solutions, and the like and is directed particularly to an expendable valve unit construction used in such surgical apparatus.

J. Wren, in U.S. Pat. No. 3,570,808 discloses a coupling assembly for releasably attaching an air hose to a regulator of the type used in conjunction with the face mask of an underwater diving apparatus. The coupling is readily detachable and a valve mechanism is provided so that when the air hose is decoupled from the regulator underwater, the valves provided in the regulator air inlet and in the end of the air hose are immediately biased to a closed position. Such a construction and arrangement might have utilization in connection with intravenous procedures.

In U.S. Pat. No. 3,599,670, J. Gurner discloses a fluid coupling with a valve means having such provision that if a maximum rate of flow through a hose is exceeded as, for example, by leakage, the coupling valve will close and prevent further flow.

In U.S. Pat. No. 3,888,249, D. Spencer discloses a catheter for prolonged infusion of medication into an artery. The catheter is provided with a tip designed employing a flap valve principle to assure uniform and steady diffusion of the medication into the blood stream and to inhibit retrograde flow of blood into the catheter thereby to minimize clotting and blockage of medication flow.

In U.S. Pat. No. 4,103,686, R. LeFevre discloses a dual valve assembly for intravenous infusions from multiple parenteral fluid sources. The assembly controls forward and reverse flow through a flow line and includes normally seated first and second valves mounted for movement toward and away from respective valve seats to control flow in such a manner as to prevent reverse flow through the assembly.

M. Gordon shows in U.S. Pat. No. 4,324,239, a safety valve for preventing air embolism and hemorrhage. The safety valve disclosed is useful for catheterization procedures and is characterized by a piston having an internal flow path and so arranged as to be biased to a closed position. The arrangement is such as to prevent air embolism and hemmorhage.

In U.S. Pat. No. 4,355,747, is disclosed an arrangement which is effective to exclude air or other undesirable gas in a connecting procedure.

None of the aforegoing patents, nor any of the other arrangements known heretofore, is effective to the same degree as the structure to be described below in the preventing of the introduction of air into the vascular system of a patient.

SUMMARY OF INVENTION

It is an object of the invention to provide an improved valve arrangement.

It is an object of the invention to provide improved arrangements for preventing air embolism or the like in connection with various intravenous procedures.

Still another object of the invention is to provide improved systems for controlling the flow of fluid, in particular, in the type of situation in which the relative negative pressure in a receiving body effectively constitutes a vacuum or suction which would tend to draw thereinto air from the ambient atmosphere.

In achieving the above and other objects of the invention, there is provided a flow control comprising a body provided with an imput chamber and an output chamber and further provided with respective orifices respectively coupled to the chambers, there being furthermore provided a resilient means associated with the aforesaid body and adapted for defining with said body a connecting channel between the orifices, but normally being configured to obturate the orifice coupled to the output chamber to obturate the latter said orifice and such that a relative negative pressure in the output chamber will tend to strengthen the obturating of the latter said orifice, whereas a relative positive pressure in the input chamber will tend to open the latter said orifice. As a result of this general type of construction, it is possible, in accordance with the invention, to prevent the drawing of air into and through the output chamber while allowing a positive pressure at the input chamber to effect a normal flow of fluid therethrough into the output chamber.

In accordance with a more specific aspect of the invention, the aforesaid resilient means encircles the above-mentioned and defines therewith, the connecting channel in the form of an annular space. The input and output chambers may, in a preferred embodiment of the invention, be coaxial bore sections with the above-mentioned orifices being radially aligned with respect thereto. The bore sections may, moreover, be parts of a common bore, with means being provided in the bore to isolate the sections from each other.

In accordance with an aspect of the invention, the above-mentioned body may be configured to define an annular groove bracketed by shoulders, said resilient means being a tube of resilient material supported on and extending between these shoulders. The control means may furthermore comprise means to urge the tube yieldingly against the orifice coupled to the output chamber. This latter said means may be, for example, a foam spring in accordance with a preferred embodiment of the invention. The foam spring may be simply a plug or body of foam such as foam rubber or a foamed plastic or the like.

In accordance with yet another aspect of the invention, the above mentioned body may include a central portion defining the above mentioned central grooves and the central portion may be of a cross-section having a flat area at which the above mentioned orifices open. Furthermore, cylindrical proportions may be connected to opposite ends of the central portion as described above.

According to yet another aspect of the invention, an intravenous system is provided comprising a source of intravenous fluid, a needle or catheter for insertion into the vascular system of a patient, a pump for performing a pumping operation and urging the fluid from the source to said catheter, catheters coupling said pump to said source and to said needle, said pump including means to terminate said pumping operation upon an opening of one of said catheters to ambient atmosphere. In conjunction with the foregoing, a flow control means is provided in at least one of the aforesaid catheters to prevent movement of air through the corresponding catheter upon an opening of the latter to ambient atmosphere.

The above and other objects, features and advantages of the invention will be apparent from the following detailed description as illustrated in the accompanying drawings.

DETAILED DESCRIPTION

This application is a continuation-in-part application of application Ser. No. 484,205, filed Apr. 12, 1983 and includes the description and drawing thereof as though embodied in entirety herein.

Figure 1:
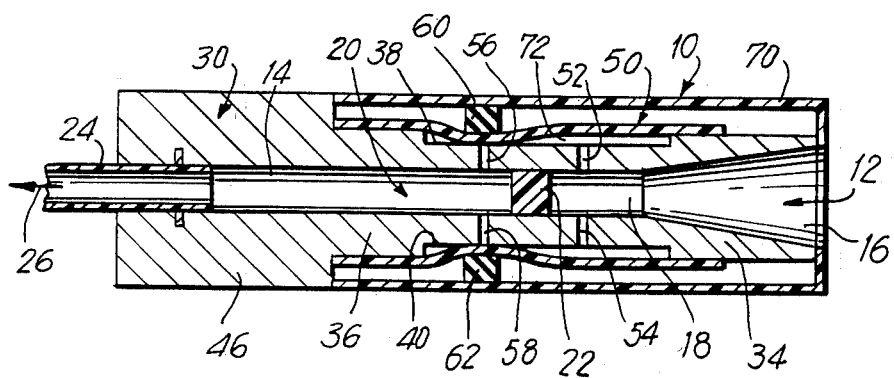
FIG. 1 is an axial cross-section of the valve provided in accordance with a preferred embodiment of the invention. The illustration being partly diagrammatic in nature.
Figure 2:
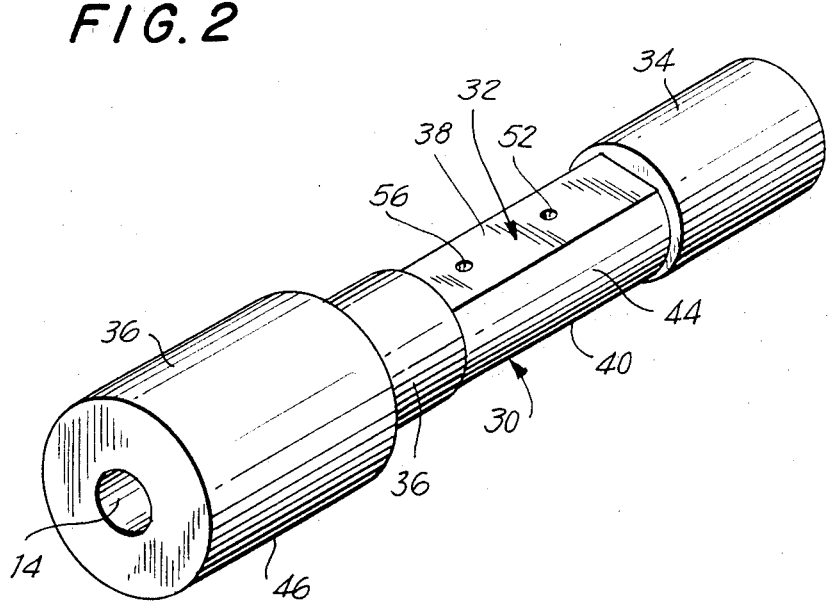
FIG. 2 is a prospective view of a portion of the construction illustrated in FIG. 1.

In FIGS. 1 and 2 is illustrated generally, a valve arrangement 10 provided with an inlet chamber 12 and an outlet chamber 14. The inlet chamber 12 comprises a conical section 16 and a bore of circular cross-section as indicated at 18. The bore section 18 is connected to a bore section constituting the outlet chamber 14. As a matter of fact, these two bore sections are parts of a common bore 20 which is preferably of circular cross-section and a continuous diameter throughout. A plug 22 of plastic may be employed to isolate the bore sections from one another for purposes to be described hereinbelow. A catheter, such as indicated at 24, may be inserted into the outlet chamber 14 to lead fluid therefrom in a direction generally indicated by arrow 26.

The bore 20, mentioned above, is defined internally within a solid relatively rigid body indicated at 30 (see also FIG. 2). This body consists of a central portion 32 mounted between and solid with two end portions 34 and 36 which are preferably cylinders of circular cross section.

The central portion 32 comprises two flat surfaces 38 and 40 onto which open the various radially disposed orifices to be detailed hereinbelow. The central portion 32 moreover comprises two curved sides one of which is visible in FIG. 2. This side is indicated at 44.

The body 30, as illustrated in FIG. 2, may further comprise the enlarged portion 46 as appears in FIG. 1. The cylindrical portions 34 and 36, however, constitute shoulders at opposite ends of the central portion. Upon these shoulders is accommodated a flexible resilient tube such as indicated at 50. This resilient tube rests upon the aforesaid shoulders and its function is to provide the selective obturating of various of the orifices as will be explained hereinafter. These orifices appear in FIG. 1 at 52, 54, 56 and 58. As has been mentioned hereinabove, these orifices are radially disposed relative to the axis of the device being described. They open on the flat surfaces 38 and 40.

In the vicinity of the orifices 56 and 58 are provided two devices 60 and 62 the purpose of which is to deform the resilient tube 50 inwardly and hold the same against the orifices 56 and 58 thereby to normally block the same. The devices 60 and 62 are effectively resilient springs and may be formed, for example, of plugs of a resilient material such as foam rubber or plastic. Their purpose is to yieldingly resist a pressure which might uncover the orifices 56 and 58 other than as described hereinbelow.

Completing the aforesaid structure is a cover tube 70 of relatively rigid material. This tube or cover may be formed of any suitable plastic.

In operation, a particular use is made of an annular space 72 which is defined by the resilient tube 50 relative to the central portion 32 of the body 30. In particular, fluid flowing into the inlet chamber 12 will pass via orifices 52 and 54 into the annular space 72 and then towards the orifices 56 and 58. The normal pressure of the fluid entering the annular chamber or space 72 will be effective to overcome the resistance of spring elements 60 and 62 thereby to uncover orifices 56 and 58. As a result, the fluid will flow into outlet chamber 14 and thence via catheter 24 in the direction indicated at 26.

Assuming that the catheter 26 is implanted into a patient, a negative pressure may appear at the downstream end of the catheter 24 thereby constituting a vacuum or negative pressure applied to the outlet chamber 14. It is desired that this negative pressure not be permitted to draw air through the valve arrangement 10 into the patient's vascular system or body. This possible activity is prevented by the fact that the normal strength of foam springs 60 and 62 will maintain the resilient tube 50 in proximity of the orifices 56 and 58 such that the suction will draw this resilient tube tightly against the orifices 56 and 62 thereby to obturate these orifices and terminate flow through the same.

Should the inlet chamber 12 be detached from the source of pressure (i.e. an infusion pump or the like) there will then be inadequate pressure to cause the fluid to oppose the action of springs 60 and 62 and the vacuum action as mentioned above will maintain orifices 56 and 58 tightly sealed whereupon it will not be possible to draw air into the outlet chamber 14. As a consequence, air flow through the catheter 24 will be automatically prevented.

Thus, there has been described a flow control which comprises a body provided with an imput chamber and an output chamber and further provided with respective orifices respectively coupled to these chambers, there being furthermore provided a resilient means associated with the body and adapted for defining with said body a connecting channel between the orifices but normally being configured to obturate the orifice coupled to the output chamber thereby to obturate the latter and such that a relative negative pressure in the output chamber will tend to strengthen the blocking of the output orifices while permitting a relative positive pressure in the input chamber to open the output orifices.

As has been described above, the resilient means is a resilient tube which encircles the above-mentioned body and defines therewith a connecting channel which is in the form of an annular space. As has also been described, the aforesaid body is configured to define an annular groove bracketed by shoulders with the resilient tube being supported on and extending between the shoulders of the body.

In intravenous procedures as may be performed in a hospital for the introduction of a fluid into the vascular system of a patient, there has never been developed a monitoring procedure which will reliably prevent the accidental detachment of a catheter. This usually results in turn in the introduction of air into the vascular system thereby causing harmful embolisms which may in fact result in death or injury to the patient being treated.

In intravenous procedures, the pressure differential between ambient atmospheric pressure and the pressure in an indwelling tube in the vascular system is normally such as to cause air bubbles to be sucked into the vascular system when the associated catheter is inadvertently opened to air. In some known systems, a commercially available pump (Valley Lab I.V. 5000B volumetric infusion pump made by Modern Medical Systems of New Hyde Park, N.Y.) is employed in such a manner that, when the system is opened to ambient atmosphere, the pump terminates its pumping operation. This provision is uniquely important in intravenous procedures, but does not prevent the inadvertent movement of air into the vascular system as may result from the aforenoted pressure differential.

Figure 3:
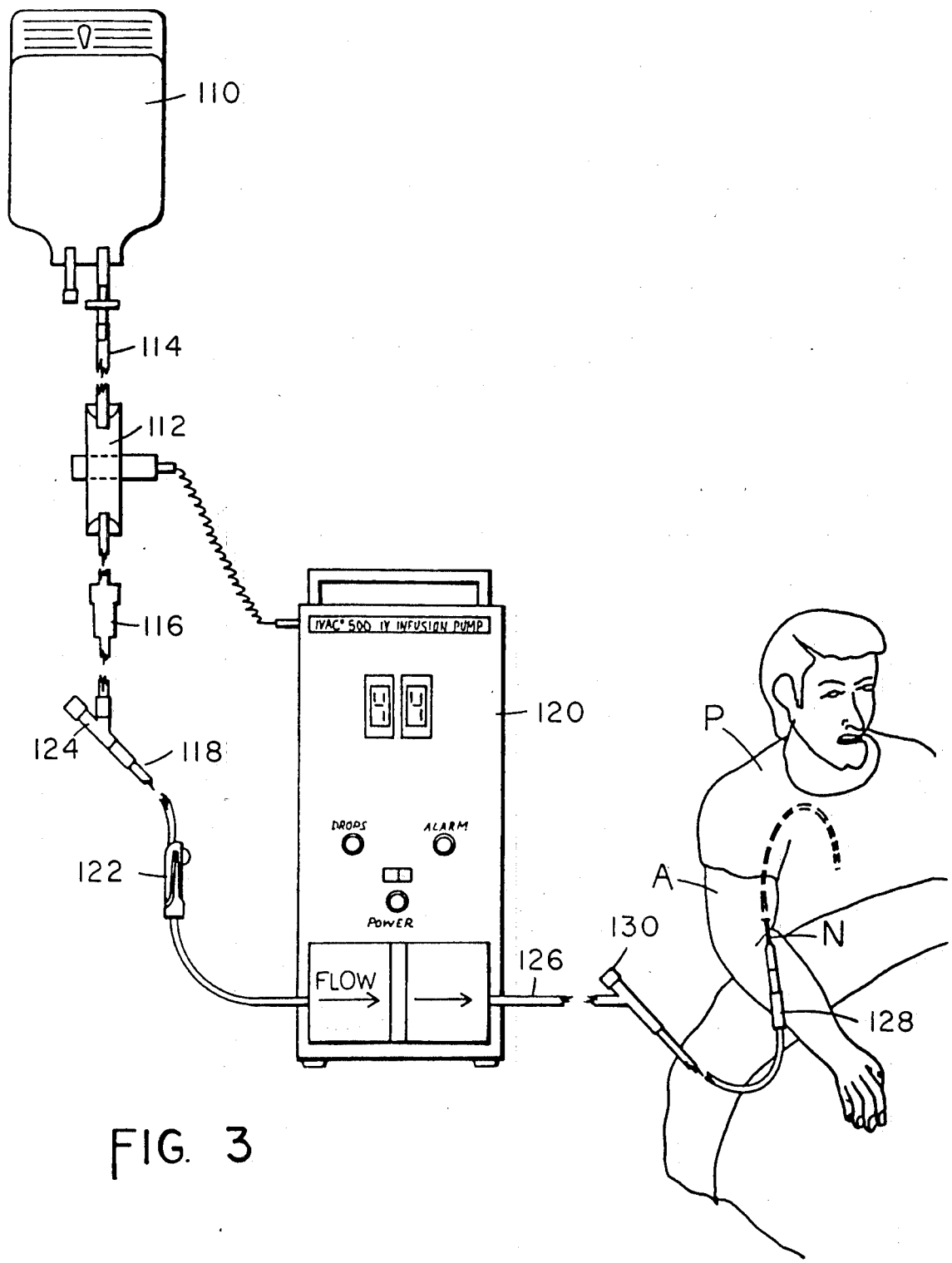
FIG. 3 is a generally pictorial partially broken away view of an intravenous procedure involving a patient and the provisions of the invention.

In FIG. 3 is indicated the physical arrangement necessary for an intravenous procedure as may be performed in a hospital or the like. The patient is indicated generally at P and into the patient's arm A is inserted a needle or catheter N through which the introduction of an intravenous fluid may be effected.

At 110 is indicated a source of intravenous fluid of known type. The source 110 is connected to a reservoir 112 via a catheter 114 with the fluid dripping downwardly drop by drop into the reservoir 112 eventually to be connected via a coupling 116 to a catheter or I.V. tubing 118 feeding into pump 120. A safety arrangement or flow control valve according to the invention may be included at 122 if desired. A spur 124 is indicated for the introduction of medical preparations, nutritional preparations or the like according to well known techniques. The pump 120 is of commercially available type which as aforesaid will terminate operation upon an occurrence of a disturbance such as the detachment of the catheter 118 from the coupling 116.

The pump 120 feeds into an intravenous tubing 126 which in turn is connected via a safety arrangement or flow control valve 128 of the invention to the in-dwelling intravenous catheter N. The tubing 126 may also be provided with a spur 130 which enables the introduction of various types of preparations into the fluid flowing to catheter 126 and via catheter or needle N into the vascular system of patient P.

The function of the safety arrangement is to permit the flow of fluid through the I.V. tubing and into the associated catheter under normal conditions wherein the fluid circuit is closed and is not open to ambient atmosphere. A further function is for this safety arrangement to provide a barrier against the penetration of air from the atmosphere due to differential negative pressure between the vascular system and ambient atmosphere as has been found sufficient to cause the sucking of air bubbles into the vascular system thereby to cause embolism or other harm to the patient being treated.

While one such system has been described in detail relative to the catheter 126 connected downstream of the pump 120 and connected to the needle or catheter N as appears in FIG. 3, it should be noted that in accordance with the invention, more than one such safety arrangement might be employed. Thus, for example, it would be preferred in accordance with the invention if a second such safety arrangement would be provided, for example, in the catheter 118 at position 122 thereby to prevent the sucking of air into the pump 120 thereby to perform in the same manner as has been indicated hereinabove.

There will now be obvious to those skilled in the art many modifications and variations of the construction set forth hereinabove. These modifications and variations will not depart from the scope of the invention if defined by the following claims.

What is claimed is:

1. A flow control comprising a body provided with an input chamber and an output chamber and further provided with respective orifices respectively coupled to said chambers, and a resilient means associated with said body and adapted for defining with said body a connecting channel between said orifices, but normally being configured to obturate the orifice coupled to the output chamber thereby to obturate the latter said orifice and such that a relative negative pressure in the output chamber will tend to strengthen the obturating of the latter said orifice whereas a relative positive pressure in the input chamber will tend to open the latter said orifice, said resilient means encircling said body and defining therewith the connecting channel in the form of an annular space, said body being configured to define an annular groove bracketed by shoulders, said resilient means being a tube of resilient material supported on and extending between said shoulders, said control further comprising spring means to urge the tube into the annular groove yieldingly against the orifice coupled to the output chamber without obstructing the orifice coupled to the input chamber so that fluid may pass into the annular groove from the orifice coupled to the input chamber before meeting resistance from said tube.

2. A flow control as claimed in claim 1 wherein said input and output chambers are coaxial bore sections and said orifices are radially aligned with respect thereto.

3. A flow control as claimed in claim 2, wherein said bore sections are parts of a common bore, comprising means in said bore to isolate said sections from each other.

4. A control as claimed in claim 1 wherein said body includes a central portion defining said annular groove, said central portion having a cross-section with a flat area at which said orifices open and being mounted between cylindrical portions making up the shoulders upon which said resilient material is supported.

5. A control as claimed in claim 4 wherein the spring means comprises a spring and wherein the control further comprises a rigid tube covering the central portion of said body and said resilient material, the spring being positioned between and pushing against the rigid tube and the resilient material respectively to effect its obturating action.

6. A control as claimed in claim 5 wherein said spring comprises a plug positioned between said rigid tube and said resilient tube in alignment with said orifice which is coupled to said output chamber, said plug normally urging said tube against said orifice which is coupled to said output chamber to block communication between said connecting channel and said orifice, said plug being deformable under pressure of fluid in said connecting channel to permit communication between said channel and said orifice which is coupled to said output chamber.

7. A control as claimed in claim 6 wherein said plug is composed of foam material.

8. A control as claimed in claim 6 wherein said plug has a flat surface seated on said flat area of said central portion.

9. A control as claimed in claim 5 wherein the body further comprises a larger cylindrical portion at one end thereof, said larger cylindrical portion defining with said rigid tube a uniform casing for said body.

10. A control as claimed in claim 6 wherein the central portion, the cylindrical portions and the larger cylindrical portion are solid with one another.

11. A control as claimed in claim 5 wherein the spring is constructed, arranged and positioned such that its obturating action will be overcome by pressures as low as the minimal pressure exerted by fluid passing through a catheter tube entering the vascular system of a human during a central venous catheterization procedure.

12. An intravenous system comprising a source of intravenous fluid, first catheter means for insertion into the vascular system of a patient, a pump for pumping fluid from said source to said catheter means, second catheter means coupling said pump to said source, said pump including means to terminate said pumping operation upon an opening of one of said catheter means to ambient atmosphere, and flow control means in at least said first catheter means for preventing movement of air therethrough, said flow control means comprising a body provided with an input chamber and an output chamber and further provided with respective orifices respectively coupled to said chambers, and a resilient means associated with said body and adapted for defining with said body a connecting channel between said orifices, but normally being configured to obturate the orifice coupled to the output chamber thereby to obturate the latter said orifice and such that a relative pressure in the output chamber will tend to strengthen the obturating of the latter said orifice whereas a relative positive pressure in the input chamber will tend to open the latter said orifice, said resilient means encircling said body and defining therewith the connecting channel in the form of an annular space, said body being configured to define an annular groove bracketed by shoulders, said resilient means being a tube of resilient material supported on and extending between said shoulders, said control further comprising spring means to urge the tube into the annular groove yieldingly against the orifice coupled to the output chamber without obstructing the orifice coupled to the input chamber so that fluid may pass into the annular groove from the orifice coupled to the input chamber before meeting resistance from said tube.

13. An intravenous system as claimed in claim 12 wherein said body includes a central portion defining said annular groove, said central portion having a cross-section with a flat area at which said orifices open and being mounted between cylindrical portions making up the shoulders upon which said resilient material is supported.

14. An intravenous system as claimed in claim 13 wherein the spring means comprises a spring and wherein the control further comprises a rigid tube covering the central portion of said body and said resilient material, the spring being positioned between and pushing against the rigid tube and the resilient material respectively to effect its obturating action.

15. An intravenous system as claimed in claim 14 wherein said spring comprises a plug positioned between said rigid tube and said resilient tube in alignment with said orifice which is coupled to said output chamber, said plug normally urging said tube against said orifice which is coupled to said output chamber to block communication between said connecting channel and said orifice, said plug being deformable under pressure of fluid in said connecting channel to permit communication between said channel and said orifice which is coupled to said output chamber.

16. An intravenous system as claimed in claim 15 wherein said plug is composed of foam material.

17. An intravenous system as claimed in claim 15 wherein said plug has a flat surface seated on said flat area of said central portion.

18. An intravenous system as claimed in claim 15 wherein the body further comprises a larger cylindrical portion at one end thereof, said larger cylindrical portion defining with said rigid tube a uniform casing for said body.

19. An intravenous system as claimed in claim 18 wherein the central portion, the cylindrical portions and the larger cylindrical portion are solid with one another.

20. An intravenous system as claimed in claim 19 wherein the spring is constructed, arranged and positioned such that its obturating action will be overcome by pressures as low as the minimal pressure exerted by fluid passing through a catheter tube entering the vascular system of a human during a central venous catheterization procedure.

21. An intravenous system as claimed in claim 12 wherein said first and second catheter means each contain the flow control means.

* * * * *